United States Patent [19]

Manginelli

[11] Patent Number: 4,936,847
[45] Date of Patent: Jun. 26, 1990

[54] REVISION KNEE PROSTHESIS

[75] Inventor: Richard P. Manginelli, Milton, Mass.

[73] Assignee: Johnson & Johnson Orthopaedics, Inc., New Brunswick, N.J.

[21] Appl. No.: 290,492

[22] Filed: Dec. 27, 1988

[51] Int. Cl.⁵ ............................................. A61F 2/38
[52] U.S. Cl. .................................................... 623/23
[58] Field of Search ...................... 623/16, 18, 20, 22, 623/23

[56] References Cited

U.S. PATENT DOCUMENTS

| | | | |
|---|---|---|---|
| 4,240,162 | 12/1980 | Devas | 623/20 |
| 4,298,992 | 11/1981 | Burstein et al. | 623/20 |
| 4,731,086 | 3/1988 | Whiteside et al. | 623/20 |

FOREIGN PATENT DOCUMENTS

| | | | |
|---|---|---|---|
| 3332354 | 3/1985 | Fed. Rep. of Germany | 623/20 |
| 2585236 | 1/1987 | France | 623/20 |

OTHER PUBLICATIONS

Surgery of the Knee, John M. Insall, Churchill Livingstone, New York, 1984, pp. 676–680.

Primary Examiner—Richard J. Apley
Assistant Examiner—David J. Isabella
Attorney, Agent, or Firm—Michael Q. Tatlow

[57] ABSTRACT

A revision knee prosthesis which includes augmentation blocks that may be added to the inferior surface of the femoral component of the prosthesis. The blocks have a post on one surface which is secured in a cavity in the inferior surface.

2 Claims, 2 Drawing Sheets

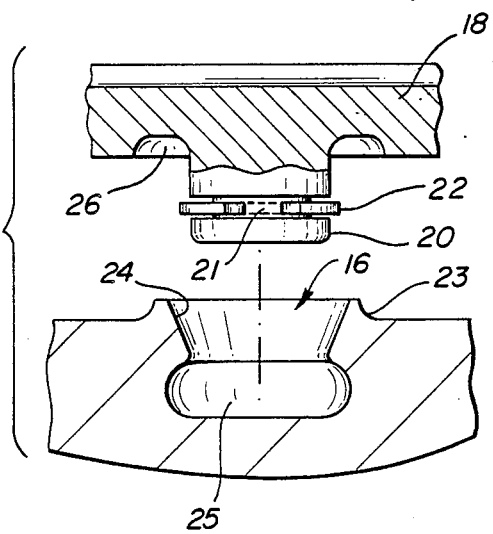
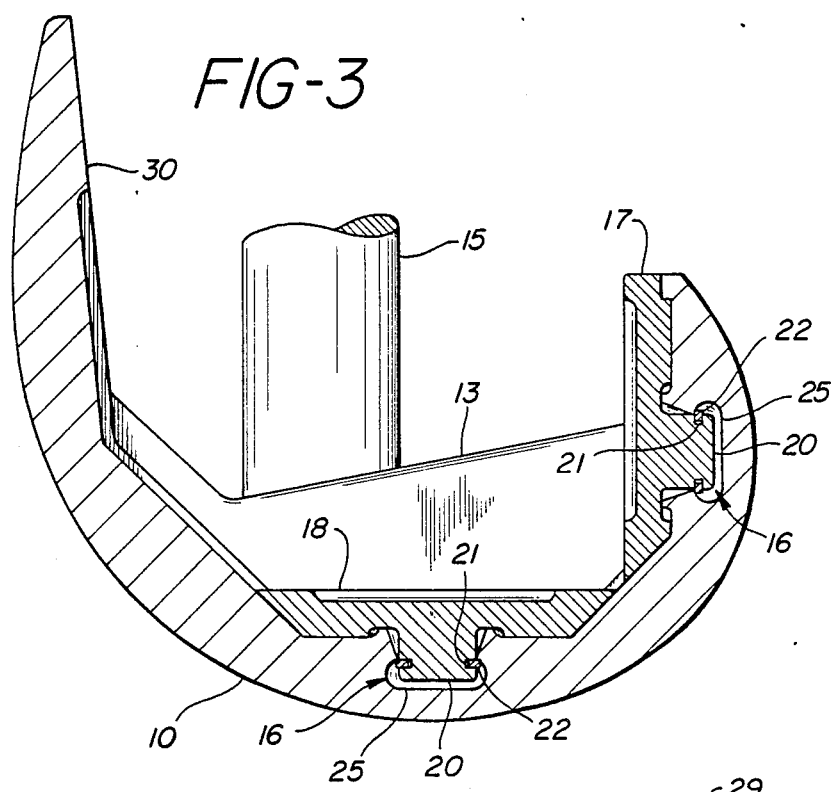
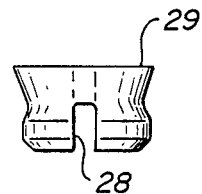

– 1 –

REVISION KNEE PROSTHESIS

FIELD OF THE INVENTION

The present invention relates to a knee joint prosthesis, and more particularly, to the femoral component of a total knee prosthesis which is particularly suitable to be used in knee revision surgery.

BACKGROUND OF THE INVENTION

The present invention relates to a knee prosthesis which is specifically designed to be used in revision surgery of previously performed knee arthroplasty. Revision surgery is performed to correct failures of previously implanted knee prosthesis. The knee prostheses fail for a number of reasons including malposition, loosening of the prosthesis, infection or dislocation. These categories are not necessarily mutually exclusive because infection, for example, may cause a loosening of the prosthesis which, in turn, might cause dislocation. When a prosthesis must be removed and a revision prosthesis inserted, it is often the case that additional bone must also be removed in order to stabilize the new prosthesis. When this occurs, the inferior portion of the femoral component of the prosthesis must be augmented to add additional thickness to compensate for the bone that has been removed. If the revision is done as a staged procedure, there is an opportunity to obtain a mold of the bone ends after the prosthesis has been removed. This allows an accurate revision prosthesis to be custom manufactured. A revision knee prosthesis could also be custom manufactured based on a construction determined through X-rays or other imaging systems.

However, it is preferable to perform the revision in a single surgical procedure. In this case, augmentation devices must be added to the femoral component during the surgical procedure. At the present time these augmentation devices are cemented into the inferior portion of the femoral component of the prosthesis. Care must be taken in accurately measuring the size of the augmentation devices because once they are cemented in position they are very difficult, if not impossible, to remove. The revision procedure is described in *Surgery of the Knee*, John M. Insall, Churchill Livingstone, N.Y. 1984, pp. 676–680.

SUMMARY OF THE INVENTION

The present invention provides a revision knee prosthesis, and particularly, the femoral component of a knee prosthesis with augmentation devices for the inferior portion of the femoral component which need not be cemented into position before they are implanted. This allows the surgeon to correctly size, i.e., the thickness of such augmentation devices using trial augmentation devices. If the trial augmentation device is too thick or too thin, it may be readily replaced with a trial augmentation device of the proper dimension and retested until the proper augmentation thickness is determined. At that time the correct thickness of the augmentation device can be selected and fitted into the femoral component.

The present invention provides a femoral component for a knee revision prosthesis which includes augmentation devices of different thickness which can be snapped into position on the inferior side of the femoral component when the surgeon has determined the desired thickness of the augmentation device. In addition, the augmentation devices of the present invention can be added to the femoral component only in those portions of the component where they are required. In addition, augmentation devices of different thicknesses can be added at different locations to the same prosthesis if required.

DESCRIPTION OF THE DRAWINGS

FIG. 2 shows a partial view, partially in section, of the augmentation device of the present invention and the cavity in the femoral component into which the augmentation device is inserted.

FIG. 3 shows a cross section of the femoral component with an augmentation device in position.

FIG. 4 shows a side view of an augmentation plug which is used to fill the augmentation cavities if an augmentation devices is not used.

DETAILED DESCRIPTION OF THE INVENTION

Figure 1:
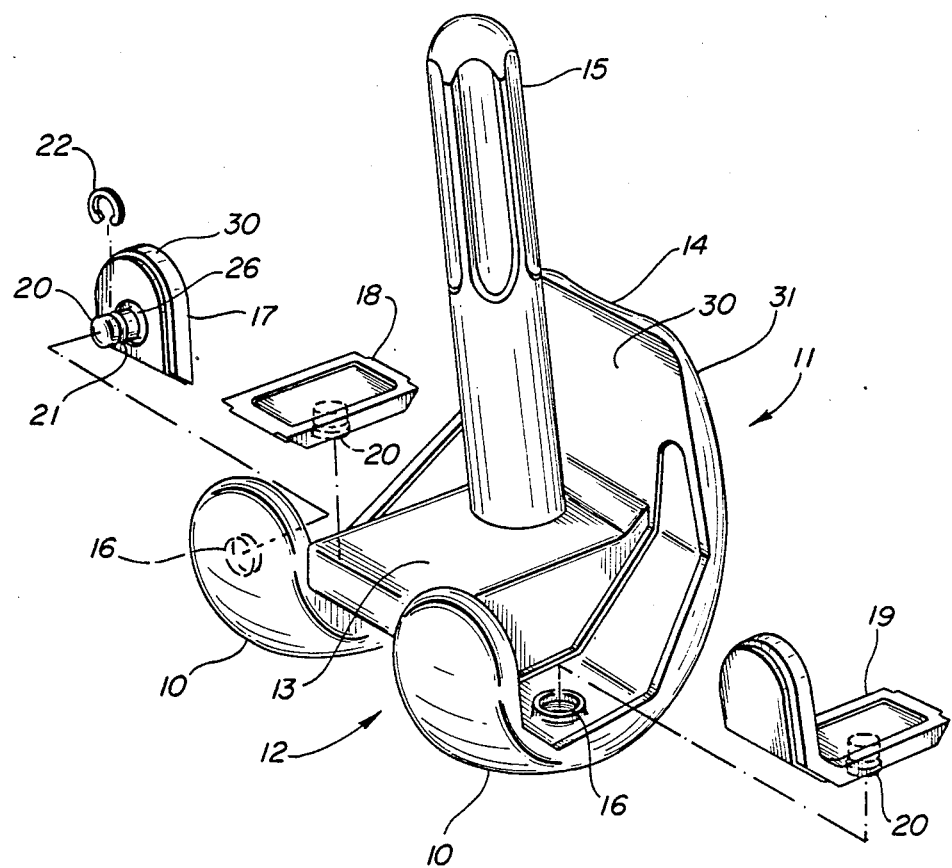
FIG. 1 shows an isometric view, partially exploded, of the femoral component with the augmentation devices of the present invention.

FIG. 1 shows an isometric view of a femoral component of a posteriorly stabilized knee prosthesis. The inner surface of the prosthesis, i.e., that surface which is affixed to the bone, is referred to as the inferior surfaces. The outer surface is referred to as the superior surface. This component is similar to the femoral component shown in U.S. Pat. No. 4,298,992. The femoral component comprises two condylar surfaces 10 having a anterior surface 11 and a posterior surface 12. The condylar surfaces are joined by a box-like intercondylar component 13. There is a depression 14 (a top of which can be seen in FIG. 1) on the superior surface of the anterior portion of the component. The patellar component of the total knee prosthesis moves in this depression when the knee is flexed. FIG. 1 also shows an optional stem 15 which may be secured to the box-like intercondylar component. This stem may or may not be used in revision surgery. The inferior portion of the femoral component, that is, the portion which will be affixed to the bone, has a series of augmentation cavities 16 on the inferior surface. These augmentation cavities are shown in greater detail in FIG. 2. The prosthesis includes a number of different, augmentation devices. These augmentation devices are used to adjust the thickness of a portion of the femoral component to compensate for bone which is removed in the revision surgery. There is a posterior condylar augmentation devices 17, a distal condylar augmentation device 18 and a combination distal and posterior augmentation device 19 that may be used with the prosthesis. Each of the augmentation devices, 17, 18 and 19 are made in different thicknesses such as 4 millimeters (mm) 6 mm and 8 mm and can be made in any thickness desired.

The outline or footprint, i.e., length and width of the augmentation devices are congruent or correspond to that portion of the inferior surface of the femoral component to which they are, affixed. As best shown in FIG. 3, the augmentation devices closely fit the configuration of the inferior surface, of femoral component. The augmentation devices are secured to the prosthesis by a mechanical interlocking device rather than by a cement. As best shown in FIG. 2, each of the augmentation devices has an augmentation post 20 which has a circumferential slot 21 around its periphery near or adjacent to its lower or distal end. This slot 21 receives a circle clip or circlip 22 which is used to hold the augmentation device in the cavity. The circlip has an opening in its circumference which allows the diameter of the clip to contract when a force is applied. The augmentation cavity has slanted walls 24 and a recess 25. There is a raised shoulder 23 at the top of the augmentation cavity and a matching recess 26 on the augmentation device to allow the augmentation device to fit snuggly into the inferior surface of the femoral component. There is an augmentation plug 27 which is used to fill the augmentation cavity when the prosthesis is manufactured. The augmentation plug contains a split region 28 at its lower end and a hole 29 that extends into the split region. The purpose of the hole 29 is to allow a tool to be inserted into the augmentation plug to pull the augmentation plug from the augmentation cavity prior to the insertion of the augmentation device into the cavity. If an augmentation device is not used on any particular position of the femoral component, the plug will not be removed from that position. The split region 28 allows the plug to flex and enter and be removed from the cavity. The plug can be made of a biologically inert plastic such as polyethylene. When the augmentation device is inserted into the cavity the slanted wall 24 forces the circlip 22, which does not extend 360° around the post, to close allowing the post 20 to pass into the recess 25. When the circlip passes the lower edge of the slanted portion of the augmentation cavity and into the recess 25, the circlip expands locking the augmentation device in place.

FIG. 1 shows separate distal condylar augmentation devices which can be inserted into one or both inferior portions of the femoral component if augmentation is needed in those regions. There is also a posterior condylar augmentation device 17 which can be inserted into the posterior condylar areas. The posterior condylar augmentation device 17 has an arcuate surface 30 which corresponds to the arcuate surface on the posterior condylar portion of the prosthesis. In addition, there are combination distal posterior augmentation devices which may be used. It should be understood that if the combination augmentation device is used, there may be only one post on the combination unit. The geometry of many prosthesis will not allow the proper fitting of a combination augmentation device with two posts. As previously indicated, these devices are made of varying thicknesses and the surgeon would select the proper thickness of the augmentation device and insert it into the femoral component during the surgical procedure. The augmentation devices are usually made of the same metal, such as chrome, cobalt or titanium, as the prosthesis or the augmentation devices can be made from a biologically inert plastic.

FIG. 3, which is a cross section of the femoral component, shows both the posterior condylar augmentation component and the distal condylar augmentation component fitted into the prosthesis. As seen in FIG. 3 that the circlips have passed beyond the slanted portion of the augmentation cavity and into the recess where they are locked into position. The recess 26 in the augmentation device allows the augmentation device to be closely fitted into the inferior surface of the femoral component.

I claim:

1. In a knee joint prosthesis having a femoral component which includes a pair of laterally spaced-apart condylar portions, each of which has a superior surface and an inferior surface and an intercondylar portion joining the condylar portions, the improvement comprising at least one augmentation cavity located on the inferior surface of a condylar portion of the prosthesis said augmentation cavity comprising a proximal opening having slanted walls and a recess at the distal end of the cavity, at least one augmentation device to adjust the thickness of a portion of the femoral component, said augmentation device having an abutting surface which is congruent to a portion of the inferior surface of the femoral component, and said abutting surface having locking means to lock the augmentation device into said augmentation cavity, said locking means including a post extending outwardly from said abutting surface, said post having a slot around its circumference and a circular clip in said slot which clip will engage a portion of said augmentation cavity to secure the augmentation device to said femoral component.

2. The prosthesis of claim 1 which comprises at least one augmentation cavity which contains a plug, said plug comprising an inert plastic material and having a split portion at its distal end to allow the plug to flex when it is forced into an augmentation cavity.

* * * * *